(12) United States Patent
Nygaard

(10) Patent No.: US 9,603,593 B2
(45) Date of Patent: Mar. 28, 2017

(54) NEEDLE HANDLING DEVICE AND A METHOD FOR IMPLANTING A PENILE PROSTHETIC INSERT

(71) Applicant: Coloplast A/S, Humlebaek (DK)

(72) Inventor: Daniel Nygaard, New Brighton, MN (US)

(73) Assignee: Coloplast A/S, Humlebaek (DK)

(*) Notice: Subject to any disclaimer, the term of this patent is extended or adjusted under 35 U.S.C. 154(b) by 0 days.

(21) Appl. No.: 14/556,248

(22) Filed: Dec. 1, 2014

(65) Prior Publication Data
US 2016/0089179 A1 Mar. 31, 2016

Related U.S. Application Data

(60) Provisional application No. 62/057,592, filed on Sep. 30, 2014.

(51) Int. Cl.
| | | |
|---|---|---|
| A61B 17/04 | (2006.01) | |
| A61F 2/26 | (2006.01) | |
| A61B 17/062 | (2006.01) | |
| A61B 17/00 | (2006.01) | |
| A61B 17/34 | (2006.01) | |

(52) U.S. Cl.
CPC .............. *A61B 17/062* (2013.01); *A61F 2/26* (2013.01); *A61B 17/0482* (2013.01); *A61B 17/3468* (2013.01); *A61B 2017/00424* (2013.01)

(58) Field of Classification Search
CPC .......... A61B 17/06109; A61B 17/0469; A61B 2017/00805; A61B 2017/06085; A61B 2017/06057; A61B 2017/0472; A61B 2017/0608

USPC .................................... 600/30, 40; 606/139
See application file for complete search history.

(56) References Cited

U.S. PATENT DOCUMENTS

| | | | |
|---|---|---|---|
| 4,244,370 A | 1/1981 | Furlow et al. | |
| 5,868,729 A | 2/1999 | Pelfrey | |
| 6,596,001 B2* | 7/2003 | Stormby | ........... A61B 17/06109 600/29 |
| 7,316,704 B2* | 1/2008 | Bagaoisan | .......... A61B 17/0057 606/213 |
| 8,118,826 B2* | 2/2012 | Zook | .................. A61B 17/3403 606/170 |

(Continued)

FOREIGN PATENT DOCUMENTS

| | | |
|---|---|---|
| DE | 2946833 A1 | 5/1980 |
| WO | 2007019016 A1 | 2/2007 |

*Primary Examiner* — Samuel Gilbert
(74) *Attorney, Agent, or Firm* — Coloplast Corp., Coloplast A/S; Nick Baumann

(57) ABSTRACT

Disclosed is a needle handling device engageable to an introducer tool used for implantation of a penile prosthetic insert in a corpora cavernosum of a penis. The needle handling device includes an attachment section, a needle capturing section and an intermediate section. The attachment section is provided at a first end of the needle handling device and is releasably attached to the introducer tool. The needle capturing section is provided at a second end of the needle handling device and is configured to capture and extract a needle out of the introducer tool. The intermediate section connects the first and the second end of the needle handling device. A method of implanting a penile prosthetic insert in a corpora cavernosum of a penis using a needle handling device is also disclosed.

15 Claims, 16 Drawing Sheets

(56) References Cited

U.S. PATENT DOCUMENTS

| | | |
|---|---|---|
| 8,545,391 B2 | 10/2013 | Rocheleau |
| 8,591,528 B2 * | 11/2013 | Devens, Jr. ........ A61B 17/0469 606/144 |
| 2004/0167574 A1 | 8/2004 | Kuyava et al. |
| 2005/0075534 A1 | 4/2005 | Kuyava |
| 2010/0160722 A1 | 6/2010 | Kuyava et al. |
| 2015/0182339 A1 * | 7/2015 | Kuyava .................... A61F 2/26 600/40 |

* cited by examiner

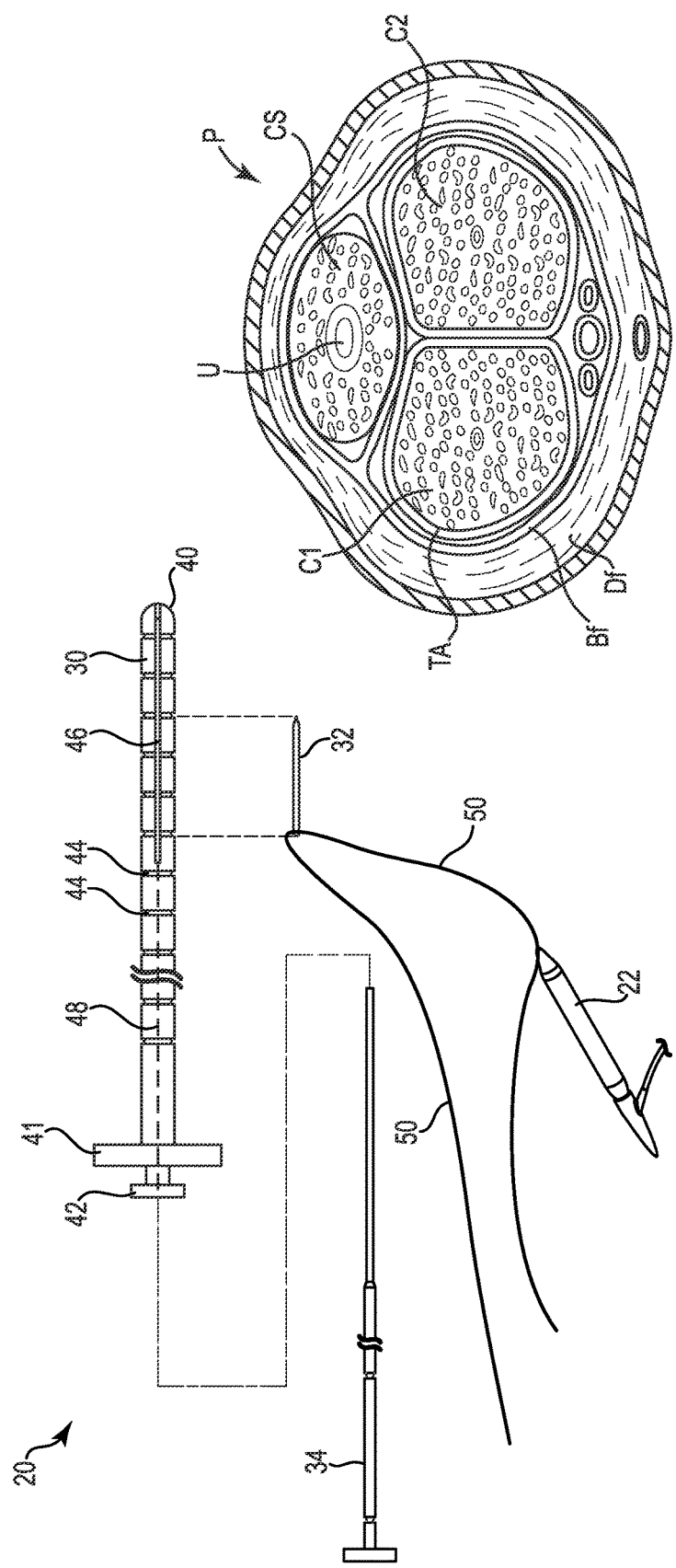

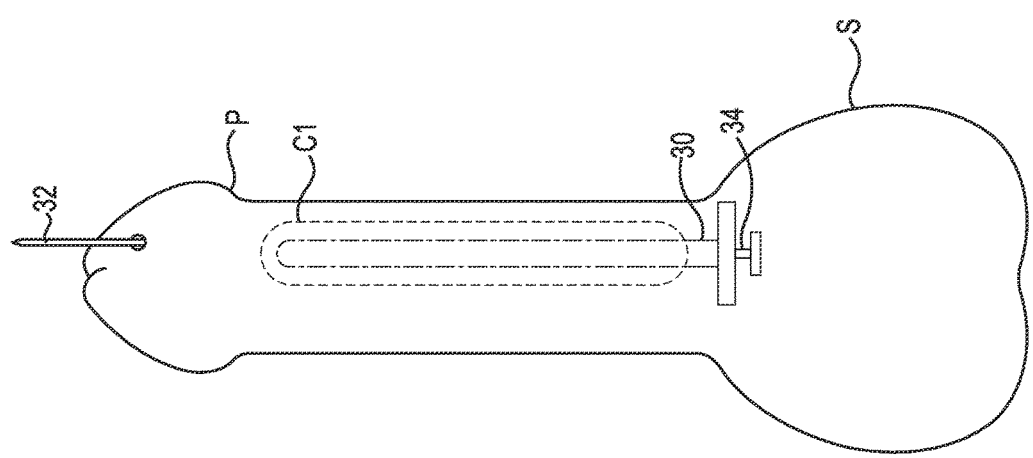

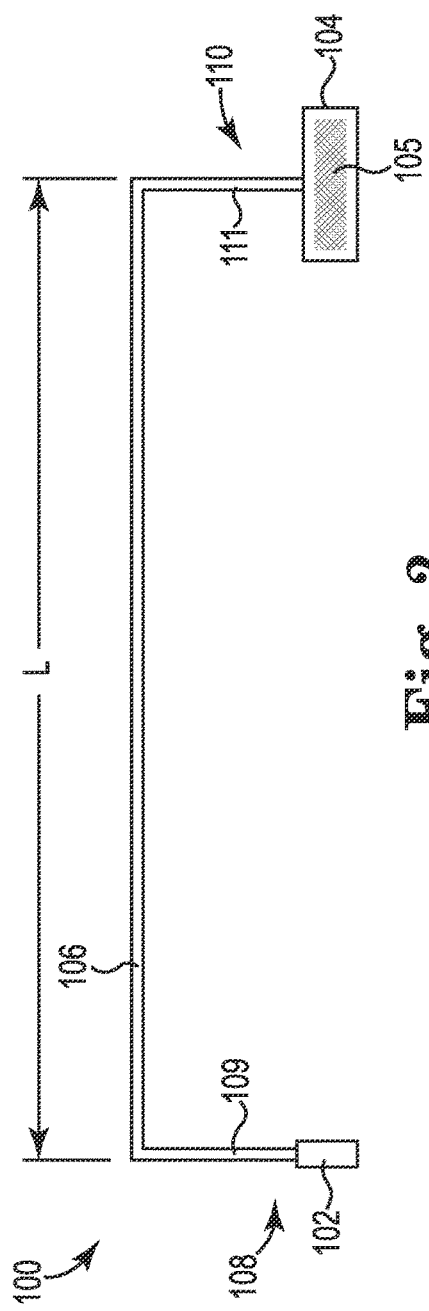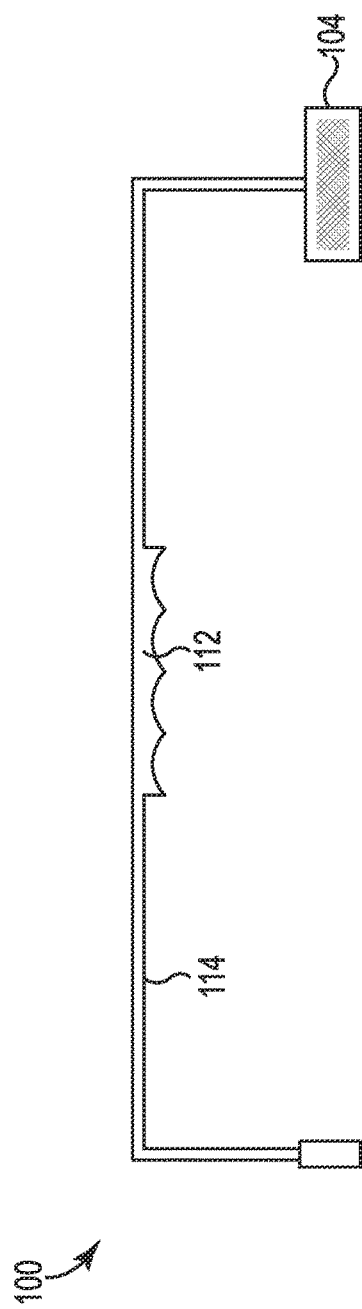

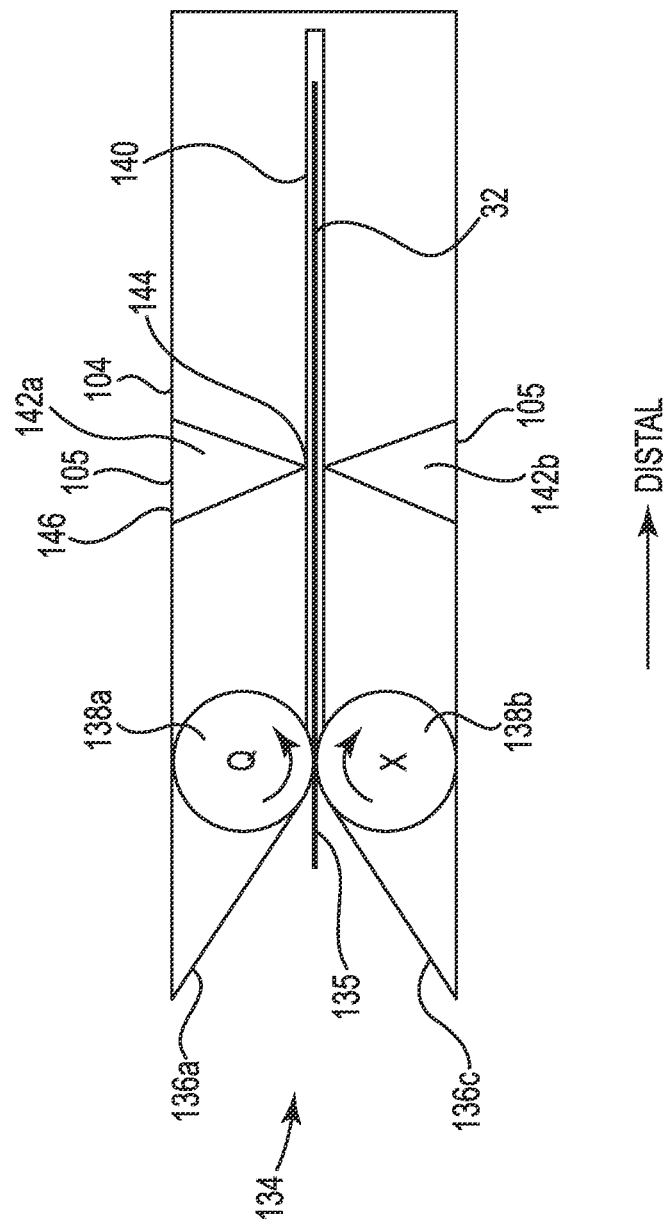

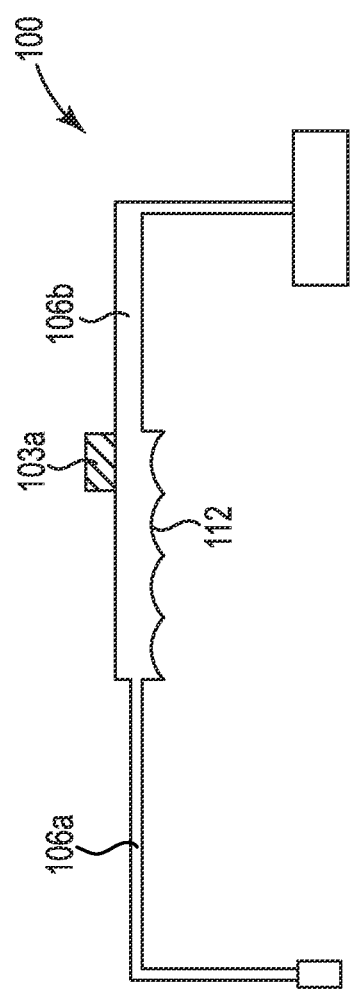
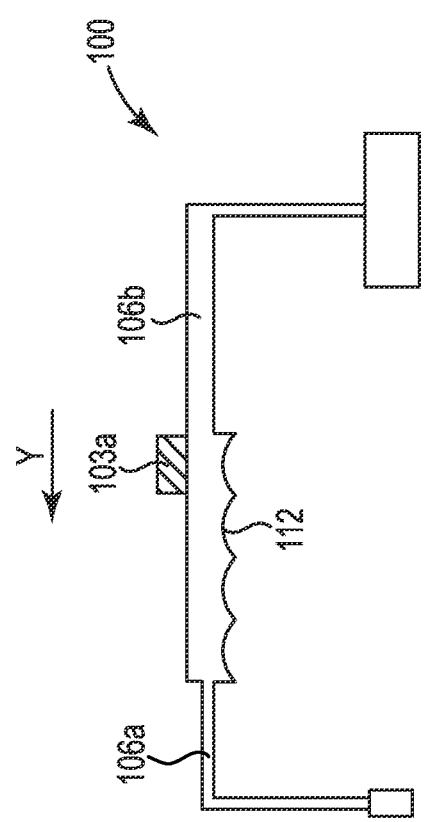
Fig. 11A
Fig. 11B

NEEDLE HANDLING DEVICE AND A METHOD FOR IMPLANTING A PENILE PROSTHETIC INSERT

BACKGROUND

An implanted penile prosthetic has proven useful in treating erectile dysfunction in men. The penile prosthetic includes two inflatable cylinders implanted in the penis, a pump implanted in the scrotum or other internal space, and a liquid holding reservoir implanted in the abdomen or other internal space.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated with an appropriate dilation tool to form a recess that is sized to receive one of the two cylinders of the penile prosthetic. Thereafter, a tool (e.g., a "Furlow" introducer) is inserted into each dilated corpora cavernosum to measure a length of the penis distally and proximally to determine a desired length of the cylinders. A cylinder of the appropriately selected length is secured to a suture, and the suture is secured to a needle that is loaded into the Furlow introducer. The Furlow introducer delivers the needle through the dilated corpora cavernosum and out the glans penis. The needle is discarded and the suture is employed to tow the cylinder into place within the dilated corpora cavernosum.

The above-described procedure has proven effective when implanting penile prostheses. However, surgeons and users would both appreciate improved tools for implanting penile prosthetic cylinders.

SUMMARY

One aspect provides a needle handling device engageable to an introducer tool used for implantation of a penile prosthetic insert in a corpora cavernosum of a penis. The introducer tool includes a barrel accommodating a needle and an obturator movable within the barrel. The obturator is configured to move the needle in a distal direction out of the barrel. The needle handling device includes an attachment section, a needle capturing section and an intermediate section. The attachment section is provided at a first end of the needle handling device and is configured to be releasably attached to the introducer tool. The needle capturing section is provided at a second end of the needle handling device and is configured to capture and extract the needle out of the barrel of the introducer tool. The intermediate section connects the first and the second end of the needle handling device.

One aspect provides a method of implanting a penile prosthetic insert in a corpora cavernosum of a penis. The method includes attaching an attachment section of a needle handling device to an exterior surface of a barrel of a penile prosthetic introducer tool where at least a distal end of the introducer tool is located in the corpora cavernosum. The method includes positioning a needle capturing section of the needle handling device distal to an exterior surface of the glans penis. The method includes moving an obturator of the introducer tool to deploy a needle out of the barrel of the introducer to penetrate through the glans penis. The method includes capturing at least a distal end of the needle in the needle capturing section of the needle handling device. The method includes releasing the needle handling device from the introducer tool. The method includes moving the needle handling device in a distal direction such that the needle is extracted entirely from the glans penis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1A is an exploded side view of a prior art tool for implanting a cylinder into a penis illustrated in FIG. 1B. FIG. 1C is a schematic top view of a penis where a prior art tool is generally located within a corpora cavernosum of a penis and a needle has been moved through the glans penis.

FIG. 2 is a side view of one embodiment of a needle handling device.

FIG. 3 is a side view of one embodiment of a needle handling device.

FIG. 9B is a top sectional view of one embodiment of the needle capturing section of the needle handling device.

FIG. 11A is a side view of one embodiment of the needle handling device in an unloaded state of a biasing mechanism.

FIG. 11B is a side view of one embodiment of the needle handling device in a loaded state of a biasing mechanism.

DETAILED DESCRIPTION

Figure 4:
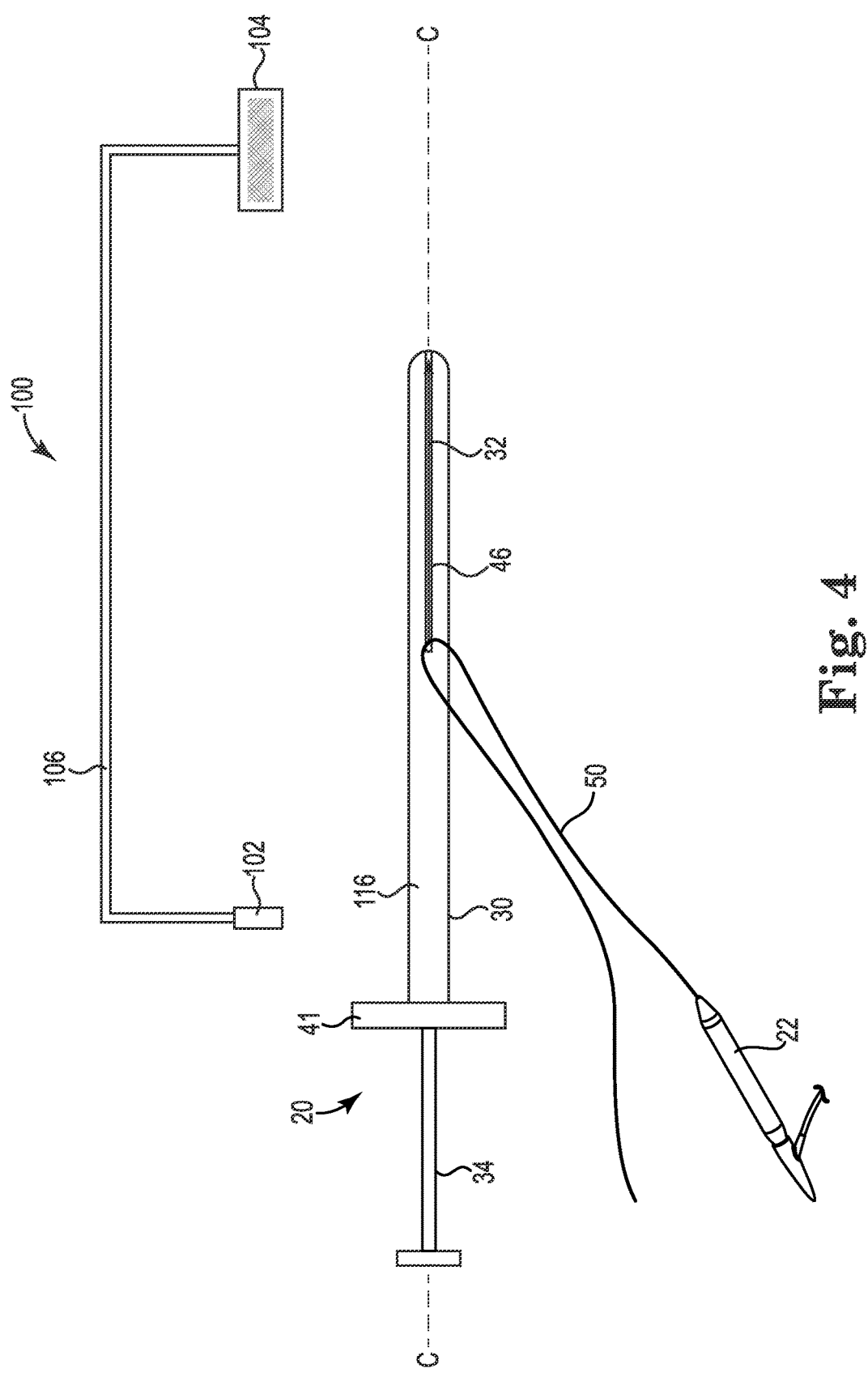
FIG. 4 is a schematic side view of one embodiment of a needle handling device ready for engagement with a penile prosthetic insertion tool.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other ("mixed and matched"), unless specifically noted otherwise.

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the crus penis of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion adjacent to the first end and another end portion adjacent to the second end.

A typical penile prosthetic includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir.

Embodiments provide a needle handling device that is attachable to a penile prosthetic insertion tool. The needle handling device includes an attachment section and a needle capturing section provided at first and second ends and connected to each other via an intermediate section. When the needle handling device is attached to an insertion tool for implanting a penile prosthetic insert, a sharp needle of the insertion tool used to penetrate the glans penis is captured and extracted by the device. The needle handling device is useful for controlling and handling the sharp needle during the surgical procedure.

Embodiments provide a method of implanting a penile prosthetic insert in a corpora cavernosum of a penis using a needle handling device that is releasably attached to a penile prosthetic insertion tool.

FIG. 1A is an exploded side view of a prior art tool 20 for implanting an inflatable cylinder 22 into a penis P illustrated in FIG. 1B. The inflatable cylinders 22 are fabricated to be pliant and comfortable when deflated and rigid and erect when inflated. The deflated cylinder 22 lacks column strength and will bend and twist and resist being pushed into the penis P. For this reason, a suture or strand is employed to pull the inflatable cylinder into place within the penis P.

The tool 20 includes a barrel 30, a needle 32 that is insertable into the barrel 30, and an obturator 34 that is insertable into the barrel 30 to push the needle 32 out of the barrel 30.

The barrel 30 extends between a curved distal end 40 and a handle 41 provided at a proximal end 42. The barrel 30 has markings 44 applied on an external surface to indicate or measure a depth to which the barrel 30 has been inserted into the corpora cavernosum. The barrel 30 is provided with a slot 46 that is sized to receive the needle 32 and a lumen 48 sized to receive the needle 32 and the obturator 34.

The needle 32 is attached to a tow suture 50 that is coupled with the cylinder 22. The tow suture 50 is generally inserted through an eyelet of the needle 32 and a hole provided at a distal end of the cylinder 22.

The obturator 34 is insertable into the lumen 48 at the proximal end 42 of the barrel 30 and operates to push the needle 32 distally out of the lumen 48.

FIG. 1B is a cross-sectional view of the penis P oriented to access by the surgeon. The surgeon gains access to the corpora cavernosa though small incisions, and with this in mind, the cross-sectional view of FIG. 1B is not the view observed by the surgeon. In the view of FIG. 1B the penis P of the patient is reclined against the body of the patient such that the urethra U, surrounded by corpus spongiosum tissue, is oriented upward.

In preparation for the implantation of the penile prosthesis, the groin area of the patient is shaved, cleaned and suitably prepped with a surgical solution prior to draping with a sterile drape as directed by the healthcare provider's procedures. A retraction device, such as a retractor sold under the trademark Lone Star and available from Lone Star Medical Products of Stafford, Tex., is placed around the penis P. A catheter is inserted into the urethra U from the distal end of the penis P into the bladder. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum.

In the transverse scrotal approach the surgeon forms a 2-3 cm transverse incision through the subcutaneous tissue of the median raphe of the upper scrotum and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access to the corpora cavernosa C1 and C2.

Each corpora cavernosum C1, C2 is dilated with an appropriate dilation tool to form a recess in the penis P that is sized to receive one of the two cylinders 22. The barrel 30 of the tool 20 is inserted into each dilated corpora cavernosum C1, C2 to measure the length of the corpora prior to selecting an appropriately sized cylinder 22. The barrel 30 is removed from the penis P. The suture 50 is inserted through the distal, leading end of the cylinder 22 and the needle 32. The needle 32 is loaded into the barrel 30 through the slot 46 and the obturator 34 is inserted into the lumen 48 via the proximal end 42 of the barrel 30. The barrel 30 is inserted into the dilated corpora cavernosum through the incision and the obturator 34 is pushed into the lumen 48 to push the needle 32 out of the barrel 30 and through the glans penis. This is illustrated in the schematic top view of FIG. 1C showing a patient's penis as it would look to a surgeon when the penis is reclined against the patient's abdominal region (i.e. with the urethra oriented upward similar to FIG. 1B). The surgeon captures the needle 32, disengages the needle 32 from the tow suture 50, and pulls on the tow suture 50 to draw the cylinder 22 into the dilated corpora cavernosum. The tow suture 50 is disengaged from the cylinder, which is now implanted within the corpora cavernosum C1 or C2.

FIG. 2 is a side view of one embodiment of a needle handling device 100 that is engageable to an introducer tool used for implantation a penile prosthetic insert in a corpora cavernosum of a penis, such as an introducer tool 20 illustrated in FIGS. 1A and 1C. In one embodiment, the device 100 includes an attachment section 102 provided at a first end 108 of the device 100, the attachment section 102 is attachable to and removable from the introducer tool 20. In one embodiment, the device 100 includes a needle capturing section 104 provided at a second end 110 of the device 100, the needle capturing section 104 operates to capture and extract a needle 32 out of a barrel 30 of the introducer tool 20. In one embodiment, the device 100 includes an intermediate section 106 connecting the first end 108 and the second end 110 of the device 100. The intermediate section 106 provides a handle surface for healthcare workers to control the device 100. In one embodiment, extender portions 109, 111 of the device 100 have equal lengths extending from the intermediate section 106 to the respective attachment section 102 and needle capturing section 104. In one embodiment, a length L of the intermediate section 106 is 15-50% longer than the penile prosthetic insert to be implanted in the patient.

In one embodiment, an exterior surface of the needle capturing section 104 includes a friction-providing pattern 105. The friction-providing pattern 105 helps provide an easy grip surface for handling and pulling of the device 100. In one embodiment, the friction-providing pattern 105 is a symmetric series of raised bumps that provide the healthcare worker with an improved grasp of the needle capturing section 104. One example of raised bumps include raised pyramids. Other acceptable raised bumps include a saw tooth pattern or a pattern of raised points. In one embodiment, the friction-providing pattern 105 is a non-symmetric matrix of raised bumps.

FIG. 3 is a side view similar to FIG. 2 showing one embodiment wherein the device 100 includes a handle portion 112 configured for one-handed gripping. In the embodiment of FIG. 3, the handle portion includes four curved segments provided in a first surface 114 of the intermediate portion 106, each curved segment configured to engage with a respective one of the index, middle, ring and little finger of one hand. Other configurations of the handle portion 112 are acceptable.

FIG. 4 is a schematic side view of one embodiment of the needle handling device 100 ready for engagement with an insertion tool 20. The insertion tool 20 is loaded with a needle 32 located in slot 46 and attached to a tow suture 50 that is also attached to a penile prosthetic insert, the insert being in form of an inflatable cylinder 22 for example. In one embodiment, the device 100 is releasably attached to the insertion tool 20. In one embodiment, the attachment section 102 attaches to an exterior surface 116 of the barrel 30. In one embodiment, the attachment section 102 attaches to the exterior surface 116 of the barrel 30 adjacent a handle 41 of the barrel 30.

Figure 5:
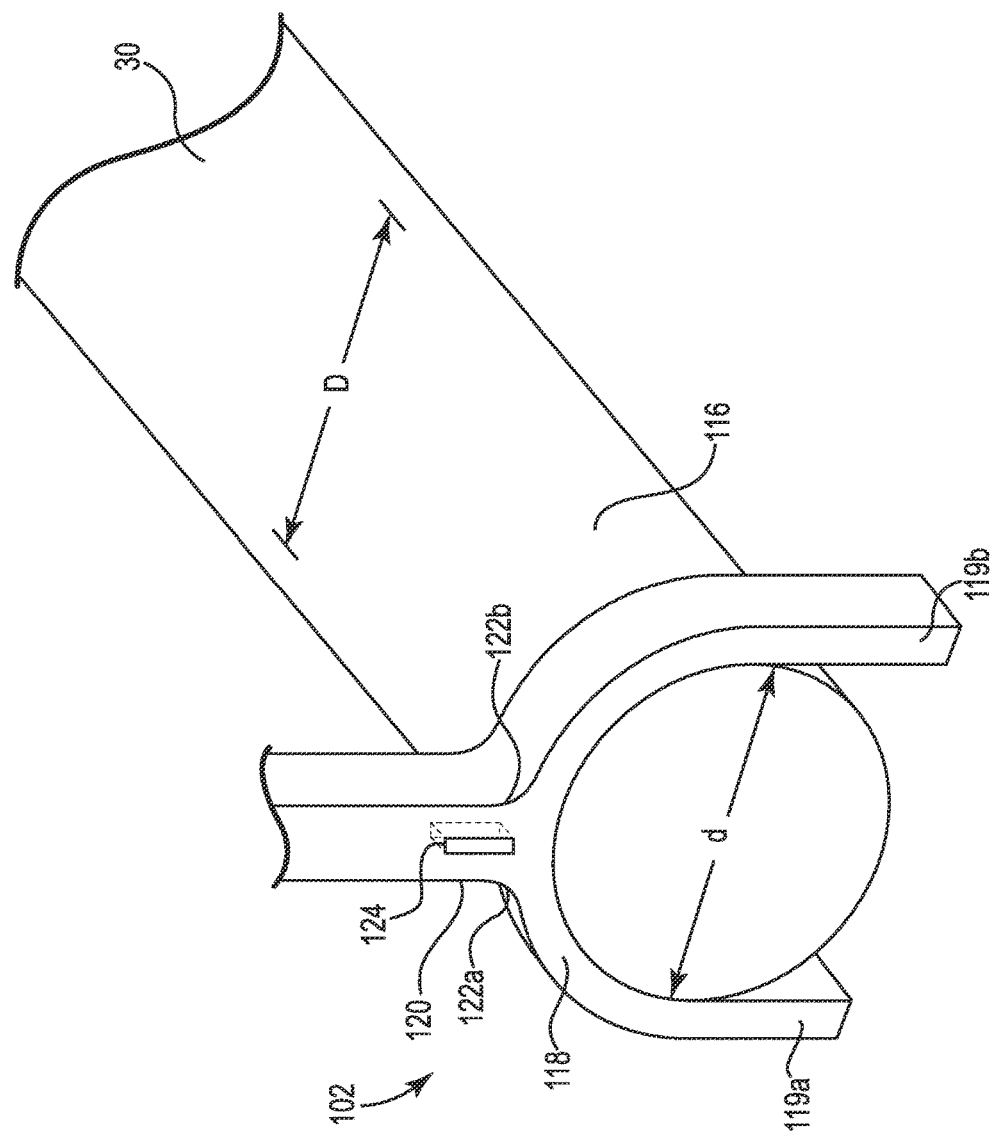
FIG. 5 is a perspective, sectional end view of one embodiment of an attachment section of a needle handling device engaged with a penile prosthetic insertion tool.

FIG. 5 is a perspective, sectional end view of one embodiment wherein the attachment section 102 includes a bifurcation 118 in which a distance d between opposing surfaces of the bifurcation is smaller than an exterior diameter D of the barrel 30. For illustration purposes, the handle 41 of the barrel 30 is not shown in FIG. 5. In one embodiment, the bifurcation 118 is sized to releasably engage in frictional relationship with the exterior diameter D of the barrel 30. In one embodiment, the attachment section 102 is fabricated to be engageable with the exterior surface 116 of the barrel 30 by providing a slight pressure with the fingers of the hand to the attachment section 102, or to the intermediate section 106 at the first end 108 of the device 100 (above the attachment section 102), so that each leg or tine 119a, 119b of the bifurcation 118 is forced slightly outward and away from the exterior surface 116 of the barrel 30. This helps provide for the bifurcation 118 and the barrel 30 to engage in a fitting, but releasable, relationship. In one embodiment, the attachment portion 102 includes a release portion 120 or a lever portion 120 that operates to pry the attachment portion 102 from the barrel 30. In one embodiment, the release portion 120 includes a set of indents 122a, 122b and a cut-out 124 provided between the indents 122a, 122b. The indents 122a, 122b provide finger engageable surfaces so that the thumb and index finger of one hand can provide a pressure to the indents 122a, 122b. The pressure causes the material of the release portion 120 at the indents 122a, 122b to locate towards the cut-out 124 which in turn forces the legs 119a, 119b of the bifurcation 118 to move slightly outward and away from the exterior surface 116 of the barrel 30. Thereby, the attachment section 102 easily releases from its engagement with the barrel 30 of the introducer tool 20. In one embodiment, a material thickness of the release portion 120 between the indents 122a, 122b and the cut-out 124 is configured such that a pressure of 1-20 Newton releases the attachment section 102.

Figure 6:
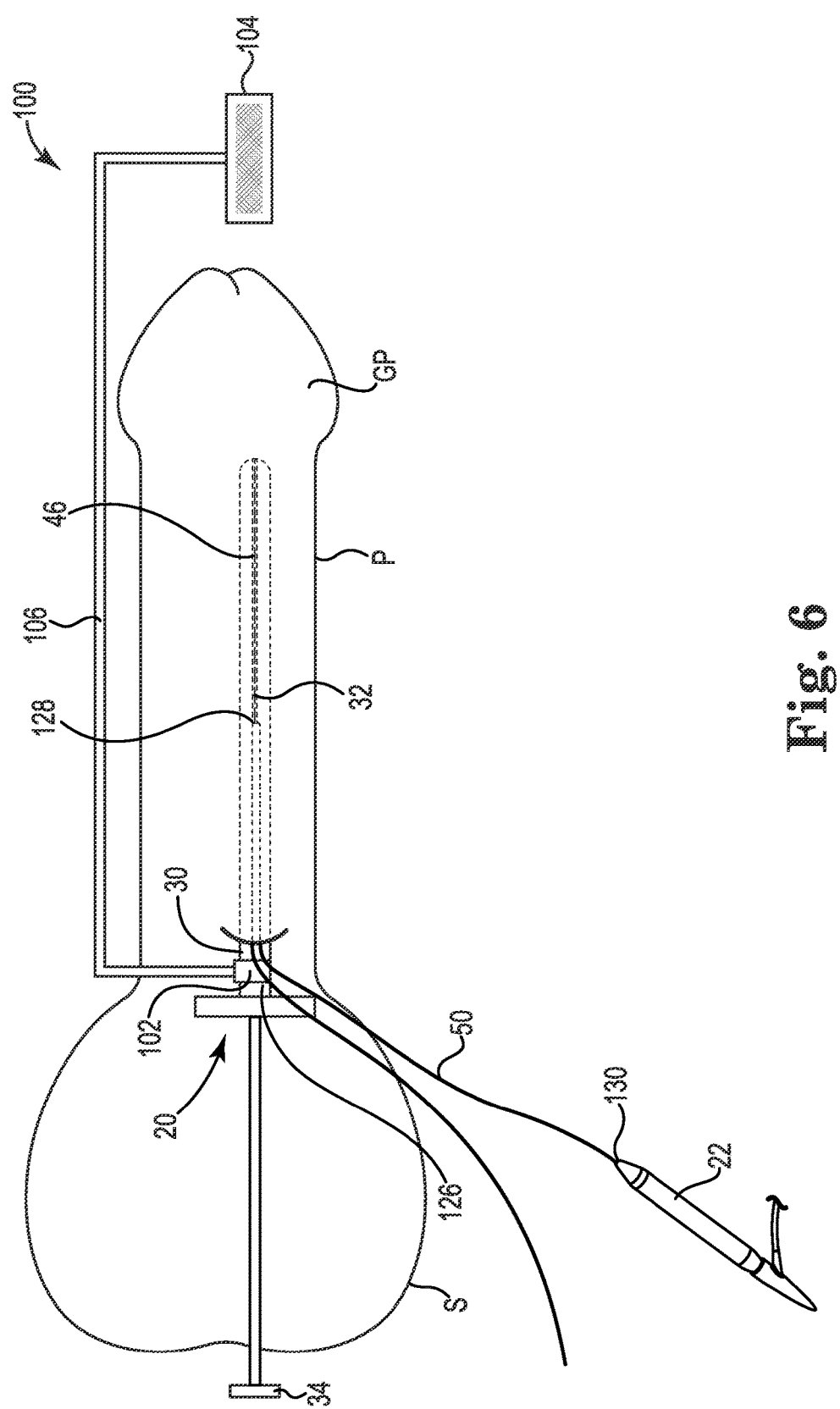
FIG. 6 is a schematic, partial cross-sectional side view of a penis P with an introducer tool in a corpora cavernosum of the penis and a needle handling device of one embodiment attached to the introducer tool.

FIG. 6 is a schematic view of a penis P in which an introducer tool 20 has been introduced into a corpora cavernosum of the penis and wherein a needle handling device 100 according to one embodiment is attached to the barrel 30 of the introducer tool 20. Most of the introducer tool 20 is shown introduced into the corpora cavernosum except for a proximal portion of the tool including the handle 41 located outside of the corpora at an incision in the patient. In one embodiment, an attachment section 102 of the device 100 is attached to an exterior surface 116 of the barrel 30 at a proximal end 126 of the barrel 30. In one embodiment, a needle capturing section 104 of the device 100 is located distal to an exterior surface of the glans penis GP. In one embodiment, the intermediate section 106 connecting the needle capturing section 104 and the attachment section 102 is provided with a linear configuration and the extender portions 109, 111 of the device 100 have the same length such that when the device 100 is attached to the introducer tool 20, the needle capturing section 104 is positioned distal to the glans penis at an axis coinciding with a center axis C (FIG. 4) of the insertion tool 20. When the needle handling device 100 is attached to the barrel 30 of the introducer tool 20, the needle capturing section 104 is separated by a distance from the barrel 30 of the introducer tool 20 and operable to capture and extract the needle 32 out of the barrel 30 of the introducer tool 20.

In one embodiment, a first segment of a tow suture 50 is attached to a trailing proximal end 128 of the needle 32 and a second segment 130 of the tow suture 50 is engaged with a proximal end portion of a penile prosthetic insert 22. In the embodiment illustrated in FIG. 6, the obturator 34 has not yet been pushed in the distal direction and the needle 32 is still sitting in the slot 46 of the barrel 30.

Figure 7:
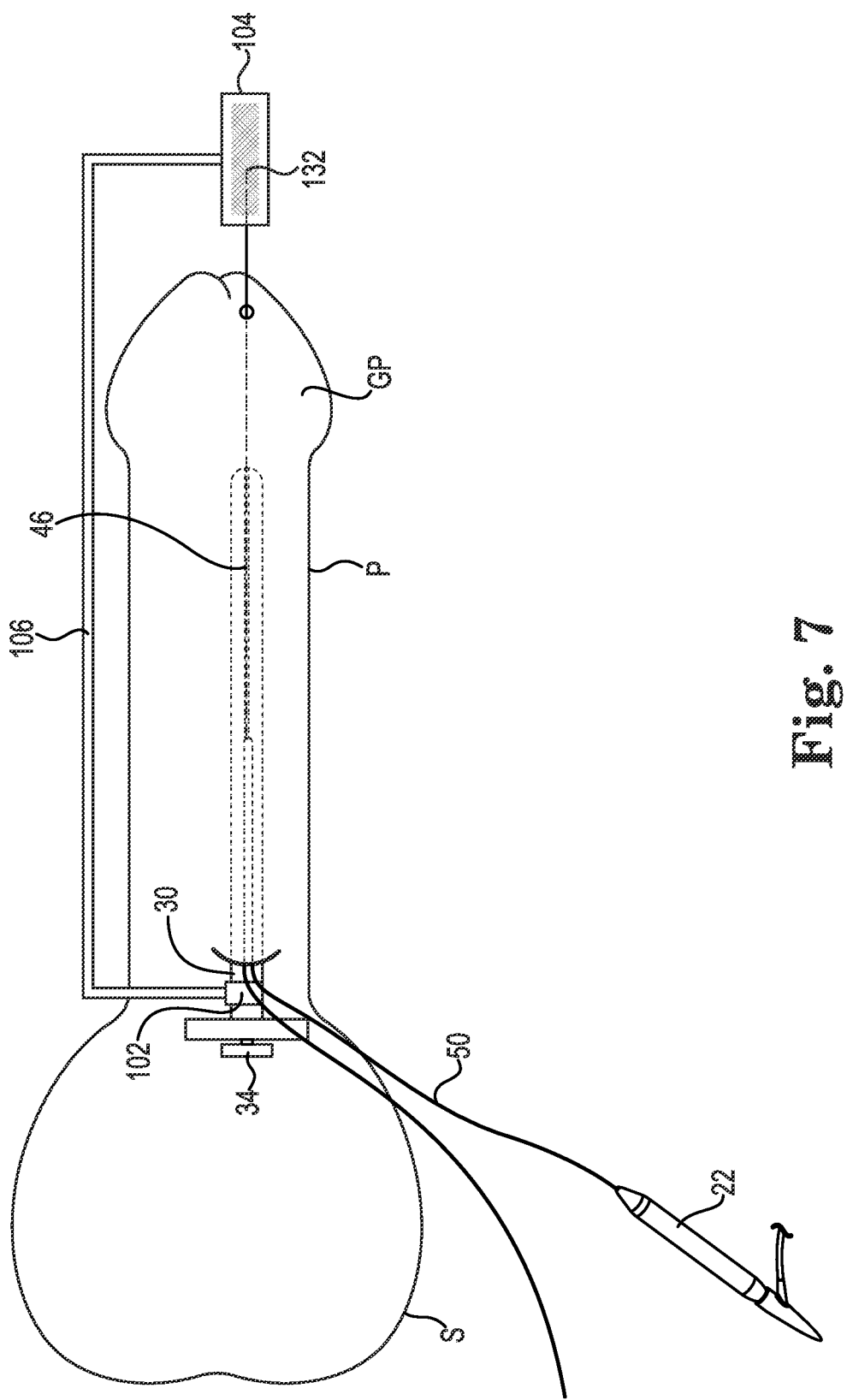
FIG. 7 is a schematic, partial cross-sectional side view similar to FIG. 6 in which a needle has been moved through the glans penis and is captured in a needle capturing section of one embodiment of a needle handling device.

FIG. 7 is a schematic view of a penis P wherein the obturator 34 has been pushed in the distal direction such that at least part of the needle 32 has deployed out of the slot 46 and has penetrated through the glans penis GP and is captured in the needle capturing section 104 of the device 100. In one embodiment, at least a pointy distal end 132 of the needle 32 is captured in the needle capturing section 104. In one embodiment, the needle capturing section is configured to receive a larger portion of the needle, such as up to and including the entire needle.

Figure 8:
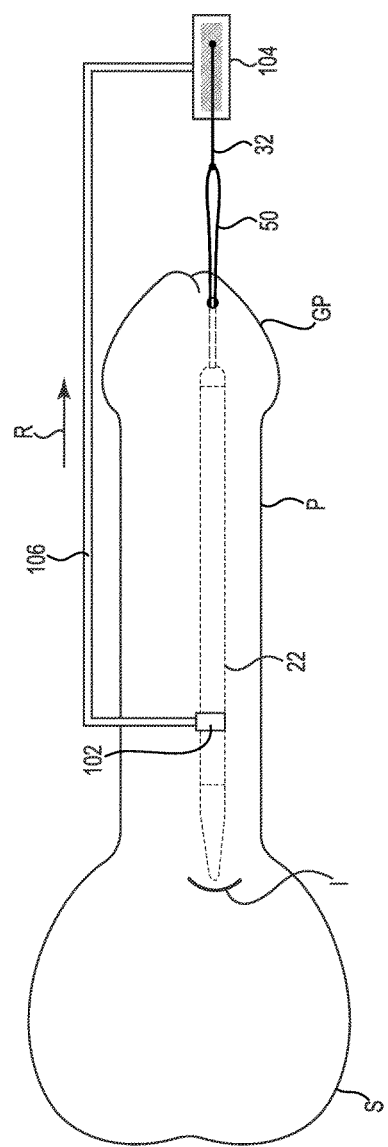
FIG. 8 is a schematic, part-sectional side view of one embodiment of a needle handling device showing a needle captured in a needle capturing section.

FIG. 8 is a schematic view of a penis P wherein the needle is moved out of the glans penis GP. In FIG. 8, the needle handling device 100 is released from its engagement with the introducer tool 20 and the introducer tool 20 (not shown) is moved in a proximal direction out of the incision I in the patient and removed. The device 100 is moved distally in the direction of the arrow R exterior to the penis P and the needle 32 captured in the needle capturing section 104 is extracted entirely from the glans penis GP. In embodiments, the suture 50 is cut from its attachment to the needle 32 such that the device 100 can be removed before pulling the suture 50 in the distal direction to pull the penile prosthetic insert 22 into position inside the corpora cavernosum. The needle handling device 100 helps provide for a controlled and safe extraction of the needle 32 from the penile prosthetic insertion tool 20 in that the needle capturing section 104 is provided at a position distal to the glans penis that is aligned with an exit position of the needle 32 through the glans penis.

In embodiments, the needle handling device 100 is moved distally along an axis substantially coinciding with a center axis of the introducer tool such that the needle is drawn through tissue of the glans penis GP in a linear motion. In one embodiment, the device 100 is moved the distal direction by pinching an exterior surface of the needle capturing section 104. In one embodiment, the exterior surface includes a friction-providing pattern 105 to be pinched and help facilitate moving the device 100. In one embodiment, the device 100 is moved in the distal direction by gripping a handle portion 112 provided in the intermediate section 106.

Figure 9A:
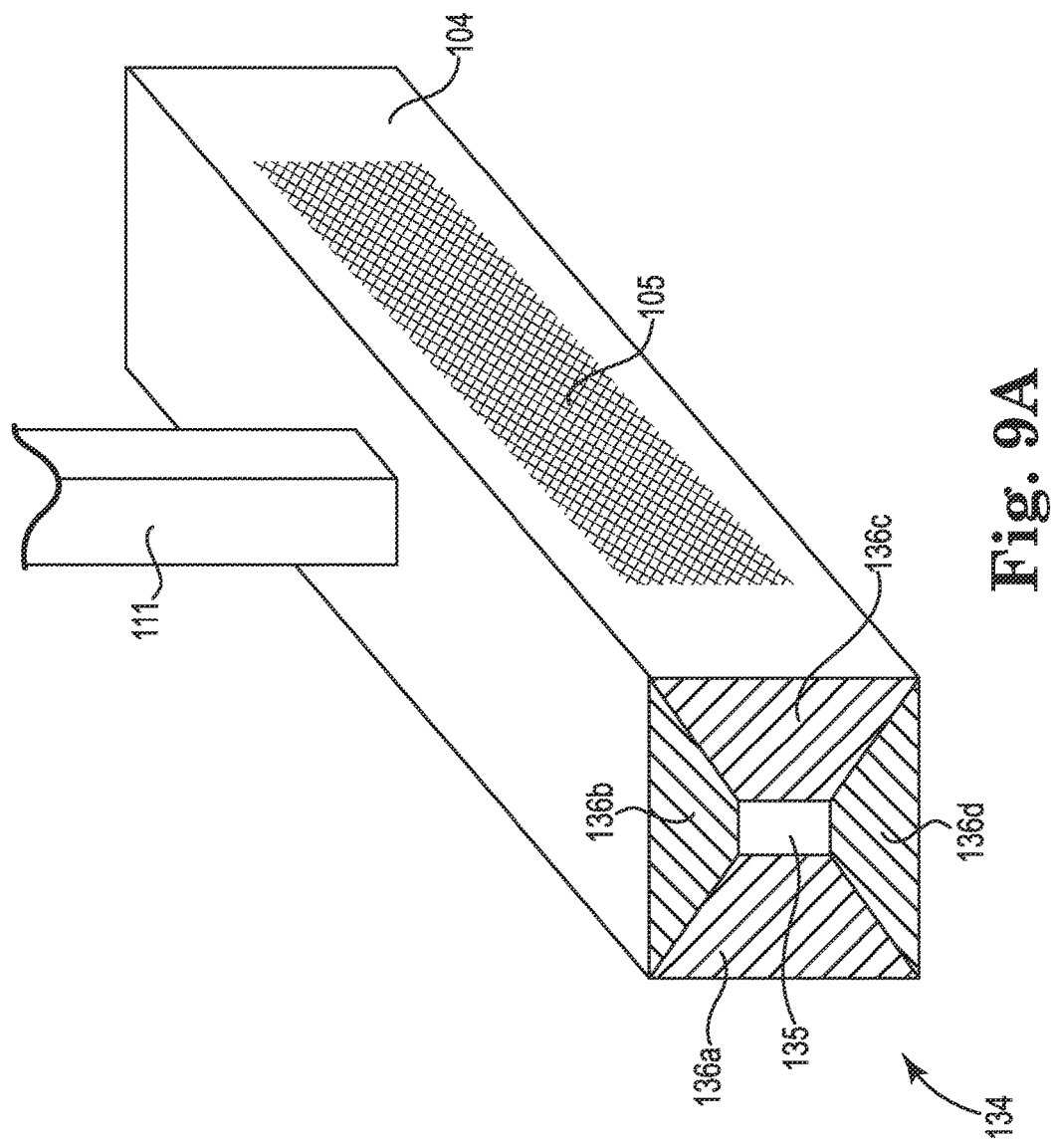
FIG. 9A is a perspective end view of one embodiment of a needle capturing section of the needle handling device.

FIG. 9A is a perspective end view of one embodiment of the needle capturing section 104 including a needle entry port 134. In one embodiment, the needle capturing section is configured to allow only one-way capturing of the needle 32 (needle not shown) through a needle entry port 134. By one-way capturing is meant that the needle 32 cannot travel in a second direction when it has entered through the needle entry port 134 in a first direction, such as by coming from a proximal direction and moving in a distal direction along a longitudinal extent of the needle capturing section 104. In one embodiment, the needle entry port 134 includes an opening 135 surrounded by four surfaces 136a-d that helps provide a lead-in for the needle. In one embodiment, the four surfaces 136a-d are inclined inwardly into the needle capturing section 104 from an outer periphery of a proximal end of the needle capturing section 104 to an inner periphery of the four surfaces 136a-d immediately surrounding the opening 135. In one embodiment, the four surfaces 136a-d provide a funnel or hopper-like guide for the needle 32 such that the needle entering the needle capturing section 104 is easily guided into and through the opening 135. In one embodiment, the needle lead-in includes a cylindrical or cone-shaped surface for guiding the needle. Other configurations of the lead-in are acceptable.

FIG. 9B is a top sectional view of one embodiment of the needle capturing section 104 including a set of opposing rolls 138a, 138b configured to receive a needle 32 between them. In one embodiment, the set of opposing rolls 138a, 138b are provided within the needle capturing section 104 immediately distal of the opening 135. In one embodiment, a first roll 138a is configured to rotate in a counterclockwise direction only (indicated by arrow Q) and a second roll 138b is configured to rotate in a clockwise direction only (indicated by arrow X). This helps provide for the rolls 138 to only allow one-way capturing of the needle 32 because when the needle 32 is engaged between the rolls 138a, 138b it can move in the distal direction only because the rolls 138a, 138b are each configured to rotate in just a single direction. In embodiments, the rolls 138a, 138b are each mounted on bearings that allow rotation of the rolls and include one or more spring-biased pin and ratchet mechanisms to allow rotation of the rolls in one direction and prevent rotation in the opposite direction (not shown) and to provide sufficient force to engage the needle 32. In one embodiment, the needle capturing section 104 includes a needle trench (or needle tubing) 140 provided inside the section 104 in continuation of the needle entry port 134. The needle trench 140 is configured to receive and guide the needle 32 inside the needle capturing section 104 when the needle 32 has passed beyond and is engaged by the rolls 138a, 138b. In one embodiment, the needle trench 140 is configured to receive the entire length of the needle 32. In one embodiment, the needle capturing section 104 includes a set of pinching spikes 142a, 142b each having a peak portion 144a, 144b engaging a side surface of the needle trench 140 and a base portion 146a, 146b wider than the peak portion 144a, 144b and engaging a wall of the needle capturing section 104. In one embodiment, the set of pinching spikes 142a, 142b is provided in the needle capturing section 104 at a position corresponding to where a friction-providing pattern 105 on an exterior surface of the needle capturing section 104 is located. Pinching of the needle capturing section 104 at the pattern 105 causes the peak portion 144a, 144b to provide pressure on the side of the needle trench 140 which in turn causes the needle 32 to be squeezed and retained in the needle trench 140. In embodiments, the needle capturing device 104 includes more than one set of opposing rolls. In embodiments, major surfaces of the rolls 138a, 138b are configured to have a friction-increasing texture for engagement with the needle 32. In one embodiment, the needle capturing section 104 includes a spring-loaded ratchet mechanism to engage with the needle to provide single direction movement. In one embodiment, the needle capturing section 104 includes a cam having a surface with a gripping texture to engage with the needle to provide single direction movement. In one embodiment, the one-way capturing of the needle is provided by applying engagement with the needle only at one side of the needle inside the needle capturing section 104.

In one example, the penile prosthetic insert includes an inflatable cylinder. In other examples, the penile prosthetic insert includes a malleable cylinder.

Figure 10A:
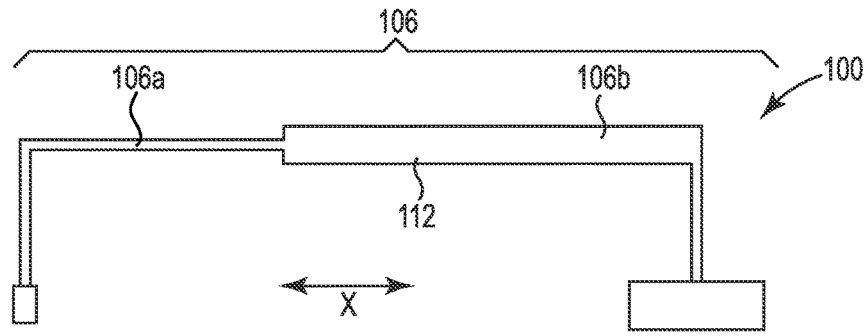
FIG. 10A is a side view of one embodiment of a needle handling device having an intermediate section including two parts.

FIG. 10A is a side view of one embodiment wherein the intermediate section 106 includes two connected parts 106a, 106b. In one embodiment, the two connected parts 106a, 106b are releasably connected to each other. In one embodiment, the two connected parts 106a, 106b are permanently connected to each other. In one embodiment, the parts 106a, 106b are movable in relation to each other (indicated by double-ended arrow X in FIG. 10A). In one embodiment, the two connected parts 106a, 106b are telescopically connected with part 106a configured to move within at least a portion of part 106b.

Figure 10B:
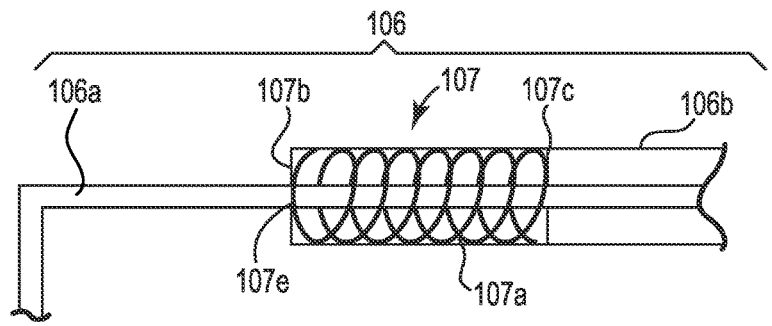
FIG. 10B is a partial, cross-sectional view of one embodiment of the needle handling device including a biasing mechanism.

FIG. 10B is a partial, cross-sectional view of one embodiment wherein the intermediate section 106 includes a biasing mechanism 107 located between the two connected parts 106a, 106b. In one embodiment, the biasing mechanism includes a spring 107a wherein, in a non-loaded state of the spring shown in FIG. 10B, a distal end of the spring 107a engages a first wall 107c of the part 106b and a proximal end of the spring is configured to engage with a second wall 107b connected to part 106b. The proximal end of the spring 107a is further attached to the part 106a at 107e such as with a collar extending around a longitudinal axis of the part 106a. A portion of the part 106a movable within part 106b is configured to extend through a space defined within the spring 107a and along at least a longitudinal extent of the spring.

Figure 10C:
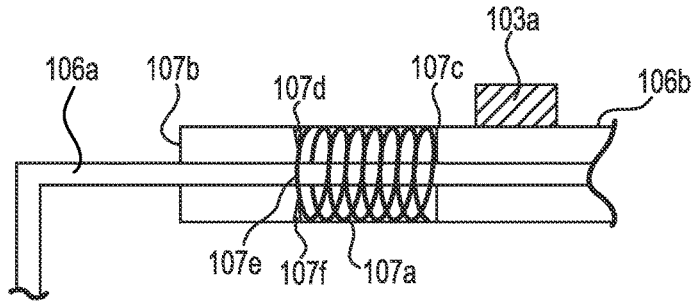
FIG. 10C is a partial, cross-sectional view of one embodiment of the needle handling device illustrated in FIG. 10B.
Figure 10D:
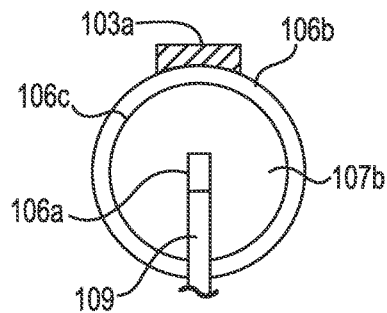
FIG. 10D is an end view of one embodiment of the intermediate section of the needle handling device.

FIG. 10C is a partial, cross-sectional view of one embodiment wherein the spring 107a is in a loaded (or armed) state. The distal end of the spring 107a is in engagement with the first wall 107c while the proximal end of the spring is engaged by a stop 107d thereby holding the spring 107a in its loaded state. The stop 107d can include one or more projections 107f extending from an internal surface of the part 106b. In one embodiment, the projections 107f are configured to nest within the internal surface when not deployed. In one embodiment, the projections 107f are configured to deploy from the internal surface when the spring 107a is moved into the biased (or loaded) state shown in FIG. 10C. In one embodiment, the biasing mechanism 107 is configured to communicate with a release button 103a located on the part 106b such that pressing the release button 103a causes the spring 107a to be released and the two connected parts 106a, 106b to be displaced in relation to each other. In one embodiment, pressing the release button 103a causes the projections 107f to retract and move away from the internal surface of the part 106b. In one embodiment, the projections 107f are configured to return to a nest position within the internal surface. In one embodiment, the release button 103a and the stop 107d are communicating via an elongated connection attached at one end to the release button and at an opposite end to the stop (not shown). Other mechanisms for making the first part 106a and the second part 106b move in relation to each other, such as but not limited to, a thumb wheel or a lever, are acceptable. FIG. 10D is a partial proximal end view of one embodiment of the needle handling device illustrating the part 106a extending out from the part 106b through wall 107b. Part 106a is connected to an extender portion 109. The release button 103a is visible on a top portion of the part 106b, but could be located at any suitable position on the part 106b. In one embodiment, the elongated connection between the release button 103a and the stop 107d (FIG. 10C) is arranged within a wall 106c of the part 106b. Other ways of making the release button and the stop communicate are acceptable.

FIG. 11A is a side view of one embodiment illustrating the needle handling device 100 and positioned in the non-loaded state of the spring 107a. In one embodiment, the release button 103a communicating with the stop 107d (not shown) of the biasing mechanism 107 is provided on the part 106b opposite to the handle portion 112. FIG. 11B is a side view of one embodiment illustrating the needle handling device positioned in the loaded state of the spring 107a (moved in the direction of arrow Y) wherein it is ready for release by pressing the release button 103a.

Figure 12A:
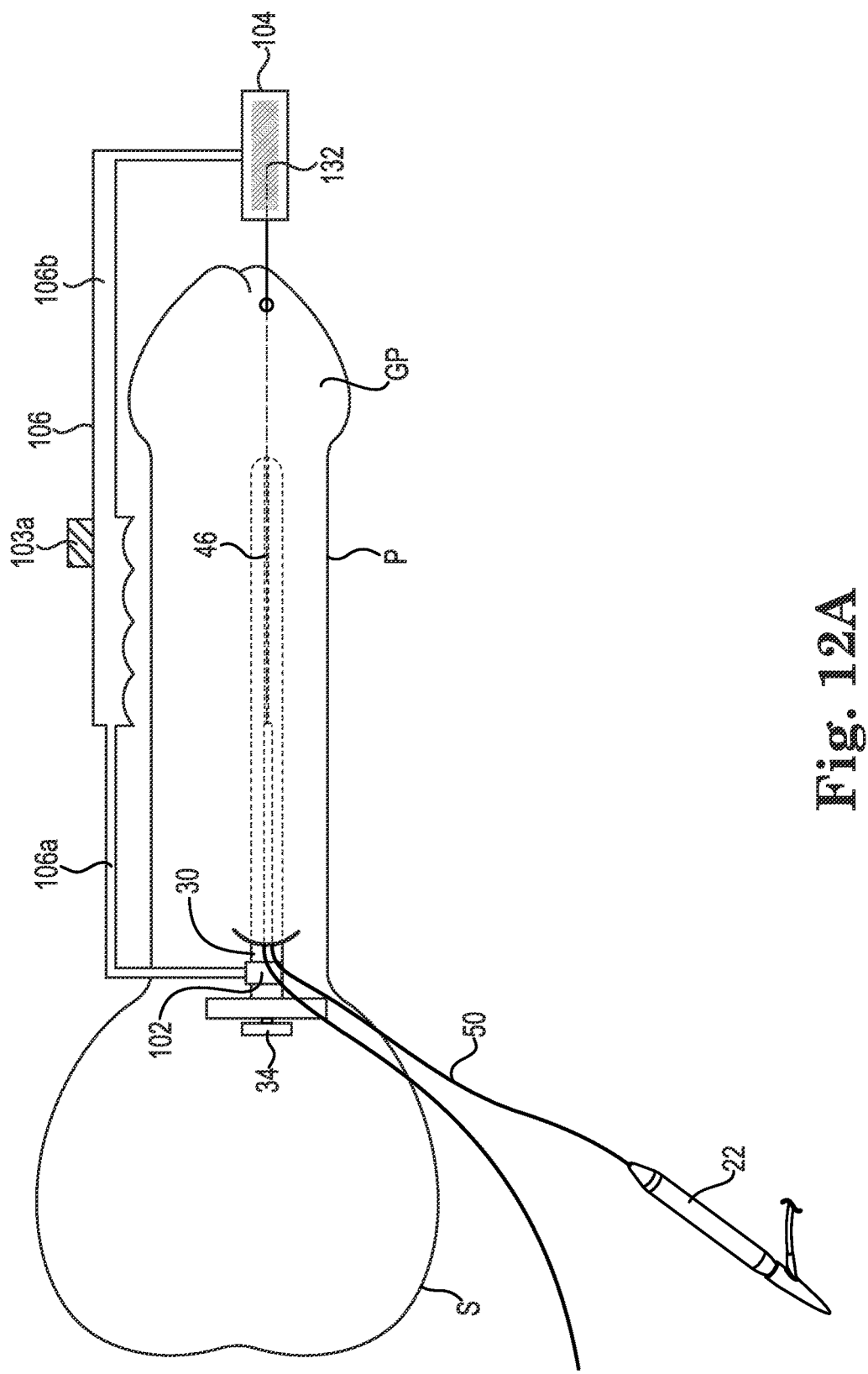
FIG. 12A is a schematic, partial cross-sectional side view of a penis with an introducer tool in a corpora cavernosum of the penis and a needle handling device of one embodiment attached to the introducer tool and configured in a loaded state of a biasing mechanism.

FIG. 12A is a schematic, partial cross-sectional view of a penis P wherein the obturator 34 has been pushed in the distal direction such that at least part of the needle 32 has deployed out of the slot 46 and has penetrated through the glans penis GP and is captured in the needle capturing section 104 of the device 100. The illustrated embodiment of the needle handling device includes an intermediate section 106 including two part 106a and 106b having a biasing mechanism 107 including a spring 107a located between them (FIGS. 10B-10C). The view of FIG. 12A corresponds to a loaded state of the spring 107a.

Figure 12B:
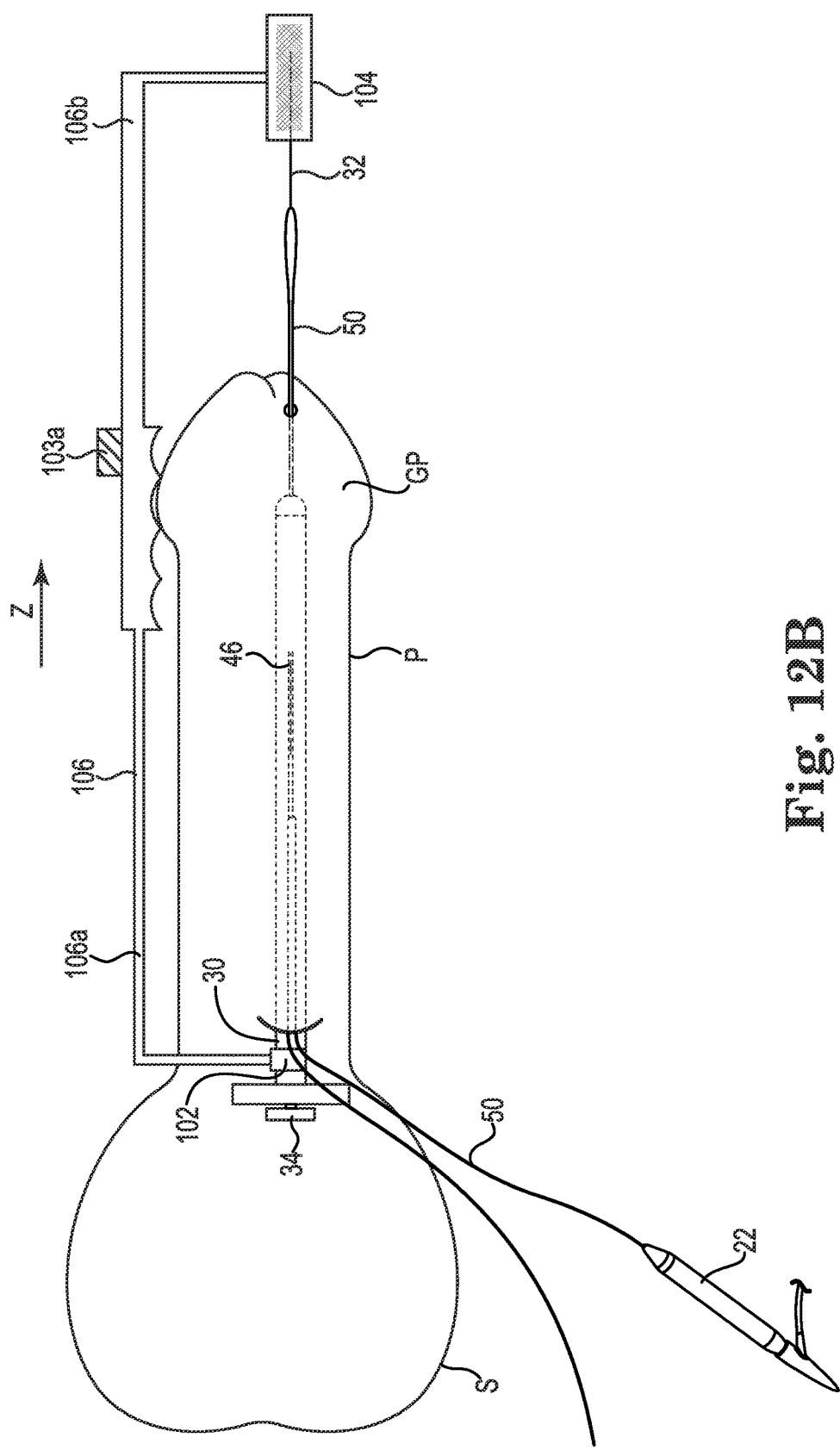
FIG. 12B is a schematic, partial cross-sectional side view of a penis with an introducer tool in a corpora cavernosum of the penis and a needle handling device of one embodiment attached to the introducer tool and configured in a unloaded state of a biasing mechanism.

FIG. 12B is a schematic, partial cross-sectional side view of a penis P corresponding to an embodiment wherein the spring 107a is in the unloaded or released state. When pressing the release button 103a communicating with stop 107d, the stop 107d disengages from the proximal end of the spring 107a and releases the spring 107a. This causes the parts 106a and 106b of the intermediate section 106 to automatically move in relation to each other and move part 106b in the distal direction (indicated by arrow Z) pulling the needle 32 through the tissue of the glans penis GP in a linear motion. This helps provide a safe and direct extraction of the needle 32 through the glans penis GP which reduces trauma on the tissue, thereby reducing the potential for tissue bleeding to the benefit of the patient and the surgical procedure.

Figure 13:
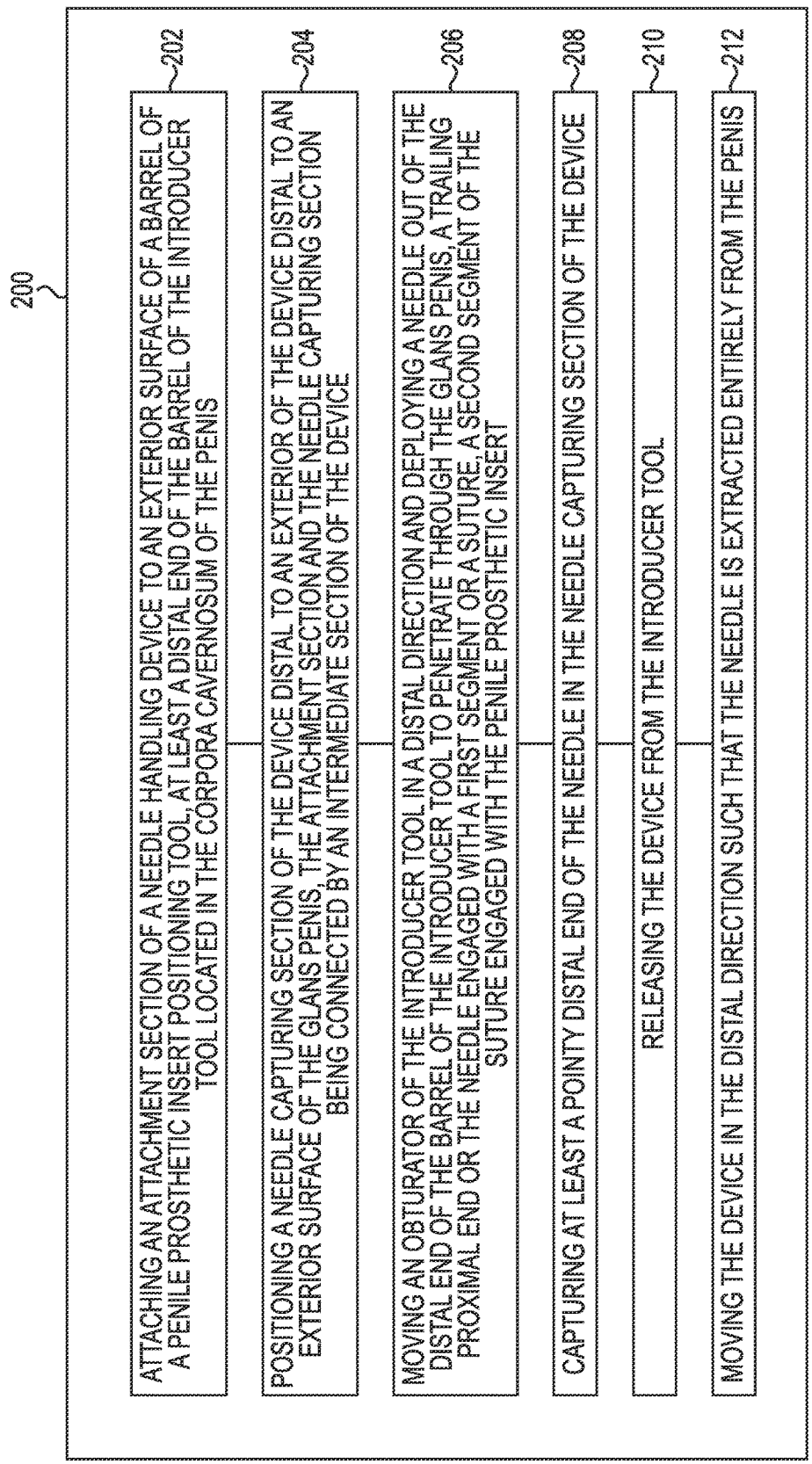
FIG. 13 is a block diagram showing one embodiment of a method of implanting a penile prosthetic insert in a corpora cavernosum of a penis.

In one aspect, the disclosure relates to a method of implanting a penile prosthetic insert in a corpora cavernosum of a penis P. FIG. 13 is a block diagram showing one embodiment of the method 200. After having prepared the patient for implantation of a penile prosthetic in a manner described above, with at least a distal end of a barrel 30 of a penile prosthetic insert introducer tool 20 being located in a corpora cavernosum of a penis P, the surgeon at 202 attaches an attachment section 102 of a needle handling device 100 to an exterior surface 116 of the barrel 30. At 204, the surgeon positions a needle capturing section 104 connected to the attachment section 102 of the device 100 via an intermediate section 106 distal to an exterior surface of the glans penis GP. At 206, the surgeon moves an obturator 34 of the introducer tool 20 in a distal direction and deploys a needle 32 out of the distal end of the barrel 30 of the introducer tool 20 to penetrate through the glans penis. A trailing proximal end 128 of the needle 32 is engaged with a first segment of a suture 50, a second segment of the suture 50 is engaged with a penile prosthetic insert 22. At 208, the surgeon captures at least a pointy distal end 132 of the needle 32 having penetrated through the glans penis in the needle capturing section 104 of the device. At 210, the surgeon releases the needle handling device 100 from the introducer tool 20. At 212, the surgeon moves the device 100 in the distal direction such that the needle 32 is extracted entirely from the penis P. In one embodiment, the step at 212 of moving the device 100 in the distal direction, includes gripping a handle portion 112 of the intermediate section 106 and moving the device 100 distally along an axis substantially coinciding with a center axis of the introducer tool 20 such that the needle 32 is drawn through tissue of the glans penis GP in a linear motion. In one embodiment, the step at 212 of moving the device 100 in the distal direction, includes pinching an exterior surface of the needle capturing section 104 and moving the device 100 distally along an axis substantially coinciding with a center axis of the introducer tool 20 such that the needle 32 is drawn through tissue of the glans penis GP in a linear motion. In one alternate embodiment, the surgeon leaves the attachment portion of the needle handling device connected to the obturator and the step of moving the device 100 in the distal direction instead includes pressing a release button 103a provided on the intermediate section 106, and communicating with a loaded spring of a biasing mechanism 107, such that a distal part 106b of the intermediate section 106 automatically moves in the distal direction and draws the needle 32 through the tissue of the glans penis GP in a linear motion.

Figure 14:
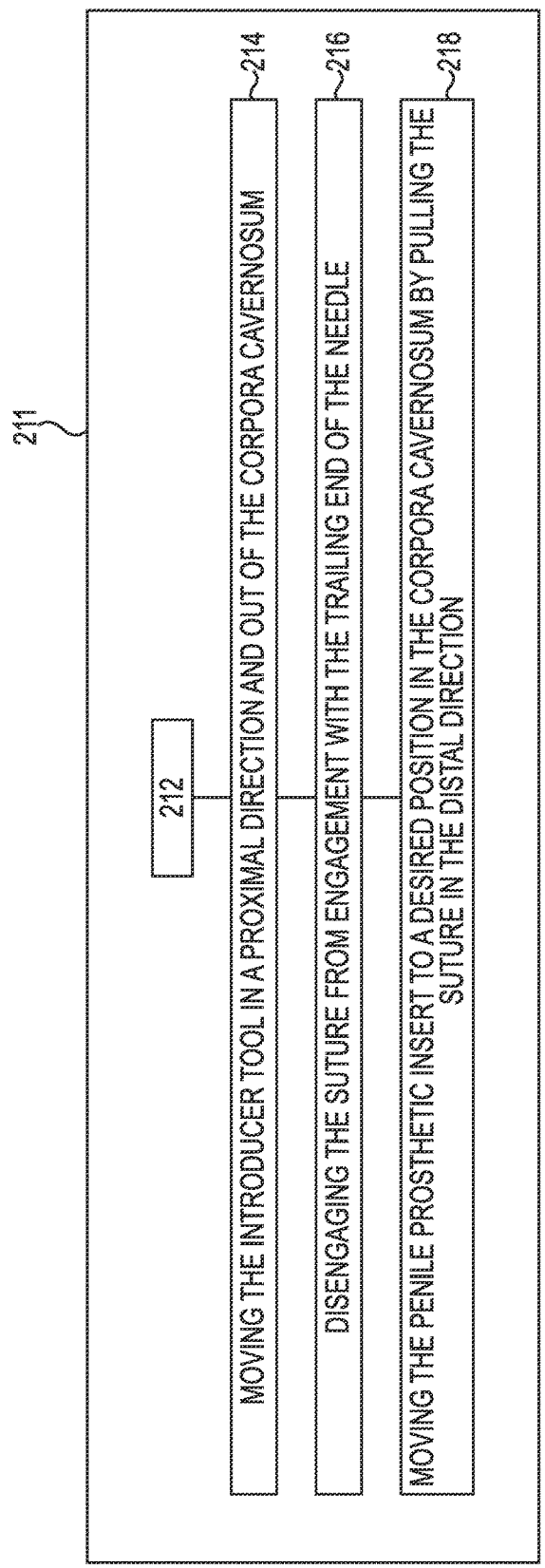
FIG. 14 is another block diagram showing one embodiment of a method of implanting a penile prosthetic insert in a corpora cavernosum of a penis.

FIG. 14 is a block diagram showing one embodiment 211 of the method of implanting a penile prosthetic insert 22. At 214, the surgeon moves the introducer tool 20 in a proximal direction and out of the corpora cavernosum. At 216, the surgeon disengages the suture 50 from engagement with the trailing end 128 of the needle 32. At 218, the surgeon moves the penile prosthetic insert 22 to a desired position in the corpora cavernosum by pulling the suture 50 in the distal direction. When the insert 22 is positioned to the satisfaction of the surgeon, the suture is removed and the incision is closed.

Embodiments described in this disclosure provide a needle handling device and an improved method of implanting a penile prosthetic insert. The needle handling device of this disclosure helps provide for controlled handling and improved safety for the staff working with the surgical procedure. Pushing the sharp needle through the glans penis could potentially expose the healthcare worker(s) to undesirable needle sticks. By providing a needle capturing section as disclosed, increased control of the penetrating needle is obtained because the needle capturing section will be located distal to and in alignment with where the sharp needle penetrates the glans penis. The needle handling device operates to extract the needle from the glans penis in a linear motion and helps provide for reduced trauma to penile tissue and thereby contributes to faster healing times to the benefit of the patient.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A needle handling device engageable to an introducer tool used for implantation of a penile prosthetic insert in a corpora cavernosum of a penis, the introducer tool configured with a barrel accommodating a needle and an obturator movable within the barrel, the obturator configured to move the needle in a distal direction out of the barrel, wherein the needle handling device comprises:

an attachment section provided at a first end of the device, the attachment section configured to be releasably attached to the introducer tool by sliding the attachment section over the introducer tool, the attachment section including a first leg portion spaced apart from a second leg portion, the first and second leg portions being configured to be forced outwardly away from one another as the attachment section is slid over the introducer tool;

a needle capturing section at a second end of the device and configured to capture and extract the needle out of the barrel of the introducer tool; and an intermediate section connecting the first end and the second end of the device;

wherein the needle capturing section comprises a set of opposing rolls configured to receive the needle between the set of opposing rolls.

2. The device of claim 1 wherein, when the needle handling device is attached to the introducer tool, the needle capturing section is separated by a distance from the barrel of the introducer tool and operable to capture and extract the needle out of the barrel of the introducer tool.

3. The device of claim 1, wherein the needle capturing section is configured to allow only one-way capturing of the needle through a needle entry port.

4. The device of claim 1, wherein the attachment section comprises a bifurcation in which a distance between inner, opposing surfaces of the bifurcation is smaller than an exterior diameter of the barrel of the introducer tool such that the bifurcation is sized to releasably engage in frictional relationship with the exterior diameter of the barrel.

5. The device of claim 1, wherein an exterior surface of the needle capturing section comprises a friction-providing pattern.

6. The device of claim 1, wherein the set of opposing rolls includes a first roll configured to rotate in a counterclockwise direction only and a second, opposite roll configured to rotate in a clockwise direction only.

7. The device of claim 1, wherein the attachment section comprises a release portion for easy releasing of the needle handling device from the introducer tool.

8. The device of claim 1, wherein the intermediate section comprises a handle portion configured for one-handed gripping.

9. The device of claim 1, wherein the intermediate section comprises a first part and a second part connected to each other.

10. The device of claim 9, wherein a biasing mechanism comprising a spring engageable between a first wall of the second part and a stop extending from an internal surface of the second part.

11. The needle handling device of claim 1, wherein the attachment section further includes a release portion operable to pry the attachment portion from the barrel of the introducer tool.

12. A needle handling device engageable to an introducer tool used for implantation of a penile prosthetic insert in a corpora cavernosum of a penis, the introducer tool configured with a barrel accommodating a needle and an obturator movable within the barrel, the obturator configured to move the needle in a distal direction out of the barrel, wherein the needle handling device comprises:
- an attachment section provided at a first end of the device, the attachment section configured to be releasably attached to the introducer tool;
- a needle capturing section at a second end of the device and configured to capture and extract the needle out of the barrel of the introducer tool; and
- an intermediate section connecting the first end and the second end of the device;
- wherein the needle capturing section comprises a set of opposing rolls configured to receive the needle between them, a first roll configured to rotate in a counterclockwise direction only and a second, opposite roll configured to rotate in a clockwise direction only.

13. A surgical system comprising:
a penile prosthetic insert for a corpora cavernosum of a penis,
an introducer tool for implanting the penile prosthetic insert into the corpora cavernosum of the penis, the introducer tool including,
a barrel,
a needle received in the barrel, and
an obturator movable within the barrel to translate the needle in a distal direction out of the barrel; and
a needle handling device including,
an attachment section provided at a first end of the device, the attachment section configured to be releasably attached to the introducer tool;
a needle capturing section at a second end of the device and configured to capture and extract the needle out of the barrel of the introducer tool; and
an intermediate section connecting the first end and the second end of the device;
wherein the needle capturing section comprises a set of opposing rolls configured to receive the needle between the set of opposing rolls.

14. The device of claim 13, wherein a length of the intermediate section is 15-50% longer than the penile prosthetic insert.

15. The device of claim 13, wherein the penile prosthetic insert is an inflatable cylinder.

* * * * *